United States Patent
Wang et al.

(10) Patent No.: US 9,937,150 B2
(45) Date of Patent: *Apr. 10, 2018

(54) METHOD FOR ENHANCING THE OXYGENATION LEVEL OF TISSUE CELLS AS AN ALTERNATIVE METHOD FOR HYPERBARIC OXYGEN THERAPY

(71) Applicant: National Sun Yat-sen University, Kaohsiung (TW)

(72) Inventors: Chia-Chen Wang, Kaohsiung (TW); Wei-Ren Chen, Kaohsiung (TW)

(73) Assignee: National Sun Yat-sen University, Kaohsiung (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/071,186

(22) Filed: Mar. 15, 2016

(65) Prior Publication Data

US 2017/0266155 A1    Sep. 21, 2017

(51) Int. Cl.
*A61K 31/365*    (2006.01)
*A61K 31/683*    (2006.01)

(52) U.S. Cl.
CPC .......... *A61K 31/365* (2013.01); *A61K 31/683* (2013.01)

(58) Field of Classification Search
CPC .................................................. A61K 31/365
USPC ........................................... 514/102
See application file for complete search history.

(56) References Cited

U.S. PATENT DOCUMENTS 9,713,602 B1 * 7/2017 Wang .................... A61K 31/343
2016/0058732 A1 * 3/2016 Wang .................... A61K 31/365
                                                        514/108

OTHER PUBLICATIONS

Venkatesh et al., J. Pharm. Sci. 89, 145-54 (2000) (p. 146, left column).*

* cited by examiner

*Primary Examiner* — Nizal S Chandrakumar
(74) *Attorney, Agent, or Firm* — Hannah M. Tien (57) ABSTRACT

The present invention relates to a method for substituting for or acting with the hyperbaric oxygen therapy to improve hypoxia, comprising the step of: administrating a phthalide compound to a subject in need thereof, wherein the phthalide compound can increase the oxygen release efficiency of blood hemoglobin (Hb) in the subject and further increase the cellular oxygenation level, and when the phthalide compound substitutes for or act with the hyperbaric oxygen therapy, the common adverse side effects of the hyperbaric oxygen therapy, such as barotrauma, decompression sickness and oxygen poisoning, are prevented. The phthalide compound is used to substitute for or act with 2,3-BPG, to modulate and decrease the oxygen affinity of hemoglobin (Hb), to increase the oxygen release efficiency of hemoglobin (Hb) to tissue cells, thereby achieving a normal cellular oxygenation level and maintaining the cellular oxygenation level in a normal range.

3 Claims, 9 Drawing Sheets

Z-butylidenephthalide     FIG. 7A

Z-ligustilide     FIG. 7B senkyunolide A     FIG. 7C senkyunolide H     FIG. 7D senkyunolide I     FIG. 7E senkyunolide F     FIG. 7F

E-butylidenephthalide     FIG. 7G

E-ligustilide     FIG. 7H 3-butylphthalide     FIG. 7I 3-butylidene-4-hydrophthalide     FIG. 7J 6,7-dihydroxyligustilide     FIG. 7K

6,7-epoxyligustilide     FIG. 7L

FIG. 8

METHOD FOR ENHANCING THE OXYGENATION LEVEL OF TISSUE CELLS AS AN ALTERNATIVE METHOD FOR HYPERBARIC OXYGEN THERAPY

FIELD OF THE INVENTION

The present invention is in the medical field, relating to a method for substituting for or cooperating with the hyperbaric oxygen therapy to improve hypoxia by using a phthalide compound.

BACKGROUND OF THE INVENTION

Hemoglobin (Hb), the oxygen-carrying protein in erythrocytes transports oxygen from respiratory organs such as respiratory tracts and lungs and releases oxygen to organs and peripheral tissues of a human body such that the organs and the peripheral tissues can be supplied with sufficient oxygen in order to maintain their normal physiological functions.

Hemoglobin of human adults is a tetramer $\alpha_2\beta_2$ consisting of four subunits, $\alpha_1$, $\alpha_2$, $\beta_1$ and $\beta_2$, wherein each subunit relies on intermolecular interactions such as intra-subunit hydrogen bonds to sustain its secondary and tertiary structures. Additionally, the inter-subunit hydrogen bonds formed among the aforementioned four subunits allow the quaternary structure of hemoglobin to be formed.

Hemoglobin can reside in two different quaternary configurations, including the relaxed form (R form) having high oxygen affinity and the tense form (T form) having low oxygen affinity. When hemoglobin is travelled to lungs through the blood circulation, hemoglobin becomes bound with oxygen and resides in the R quaternary configuration of high oxygen affinity. The oxygenated hemoglobin is then transported to organs and peripheral tissues through blood circulation and releases oxygen to organs and peripheral tissues and transforms into the T quaternary configuration of low oxygen affinity. The allostery of hemoglobin is also influenced by several allosteric factors, such as the pH value, the carbon dioxide concentration and the 2,3-BPG concentration in erythrocytes.

2,3-bisphosphorglycerate (2,3-BPG, or 2,3-diphosphoglycerate (2,3-DPG), hereinafter "2,3-BPG") is the endogenous allosteric effector of hemoglobin and the most important chemical species in an erythrocyte of a human body besides the oxygen-carrying entity, hemoglobin. 2,3-BPG delicately regulates the configuration of hemoglobin by interacting with the $\beta_1$ and $\beta_2$ subunits of hemoglobin to stabilize hemoglobin in the low oxygen affinity T form to reduce the oxygen affinity of hemoglobin, thereby facilitating hemoglobin to effectively release oxygen to body organs and tissue cells.

The conventional hyperbaric oxygen therapy is to place a patient in a hyperbaric chamber, wherein the chamber is pressurized and maintained at 2.0-3.0 atmospheres, while the patient inhales 100% oxygen through an oxygen mask to increase blood oxygen concentration, thereby improving the hypoxia, promoting wound healing or treating acute hypoxia conditions.

However, the hyperbaric oxygen therapy may cause considerable adverse side effects, including barotrauma, decompression sickness and oxygen poisoning, which can at times become fatal if improperly operated, because the patient inhales a high concentration of oxygen under the high pressure, which may lead to rapid pressure changes among tissues.

SUMMARY OF THE INVENTION

The present invention relates to a method for substituting for or cooperating with the hyperbaric oxygen therapy to improve hypoxia by using a phthalide compound, wherein the phthalide compound can increase the oxygen release efficiency of hemoglobin (Hb) which further increases the oxygenation level of tissue cells, and when the phthalide compound is administered to a patient to substitute for or to act together with the hyperbaric oxygen therapy, the common adverse side effects of the hyperbaric oxygen therapy, such as barotrauma, decompression sickness and oxygen poisoning, are prevented. The phthalide compound is used to substitute for or to cooperate with 2,3-BPG, to modulate and decrease the oxygen affinity of hemoglobin (Hb), to increase the oxygen release efficiency of hemoglobin (Hb) to tissue cells, thereby achieving a normal cellular oxygenation level and maintaining the cellular oxygenation level within a normal range.

DETAILED DESCRIPTION OF THE INVENTION

Therefore, the present invention provides a method for substituting for or adjunctly acting with the hyperbaric oxygen therapy to improve hypoxia by using a phthalide compound, comprising the steps of: administering to a subject in need thereof a phthalide compound, wherein the phthalide compound has an effect of increasing the oxygen release efficiency of hemoglobin (Hb) of the subject and the subject in need thereof is a subject treated by the hyperbaric oxygen therapy or a subject who needs to be treated by the hyperbaric oxygen therapy, wherein the phthalide compound has the effect of increasing the oxygen release efficiency of hemoglobin (Hb) of the subject treated by the hyperbaric oxygen therapy. The method of the present invention is to increase oxygenation level of tissue cells and to treat/alleviate hypoxia by reshaping oxygen equilibrium curves for hemoglobin (Hb) without excessively increasing the oxygen partial pressure, thereby preventing the adverse side effects of the hyperbaric oxygen therapy. The phthalide compound is used to substitute for or act together with 2,3-BPG in the treated subject to increase the oxygen release efficiency of hemoglobin (Hb) to tissue cells, and thus the oxygenation level of tissue cells is increased and the hypoxia is alleviated while the oxygen partial pressure is not altered or excessively increased.

Figure 8:
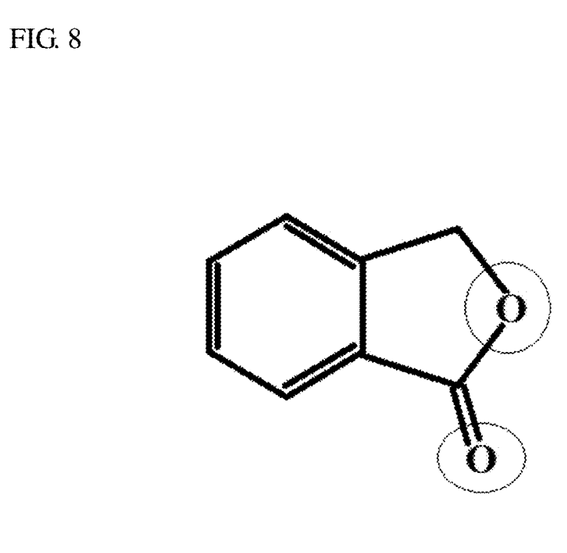
FIG. 8 is a diagram, showing the molecular structure of the functional groups of the phthalide compound.

The phthalide compound of the present invention is any compound which exhibits the structural characteristics of the functional groups of phthalide compounds as shown in FIG. 8, wherein the circled areas are the functional groups of the phthalide compounds characterized by an endocyclic oxygen and an adjacent ketone group.

Figure 1:
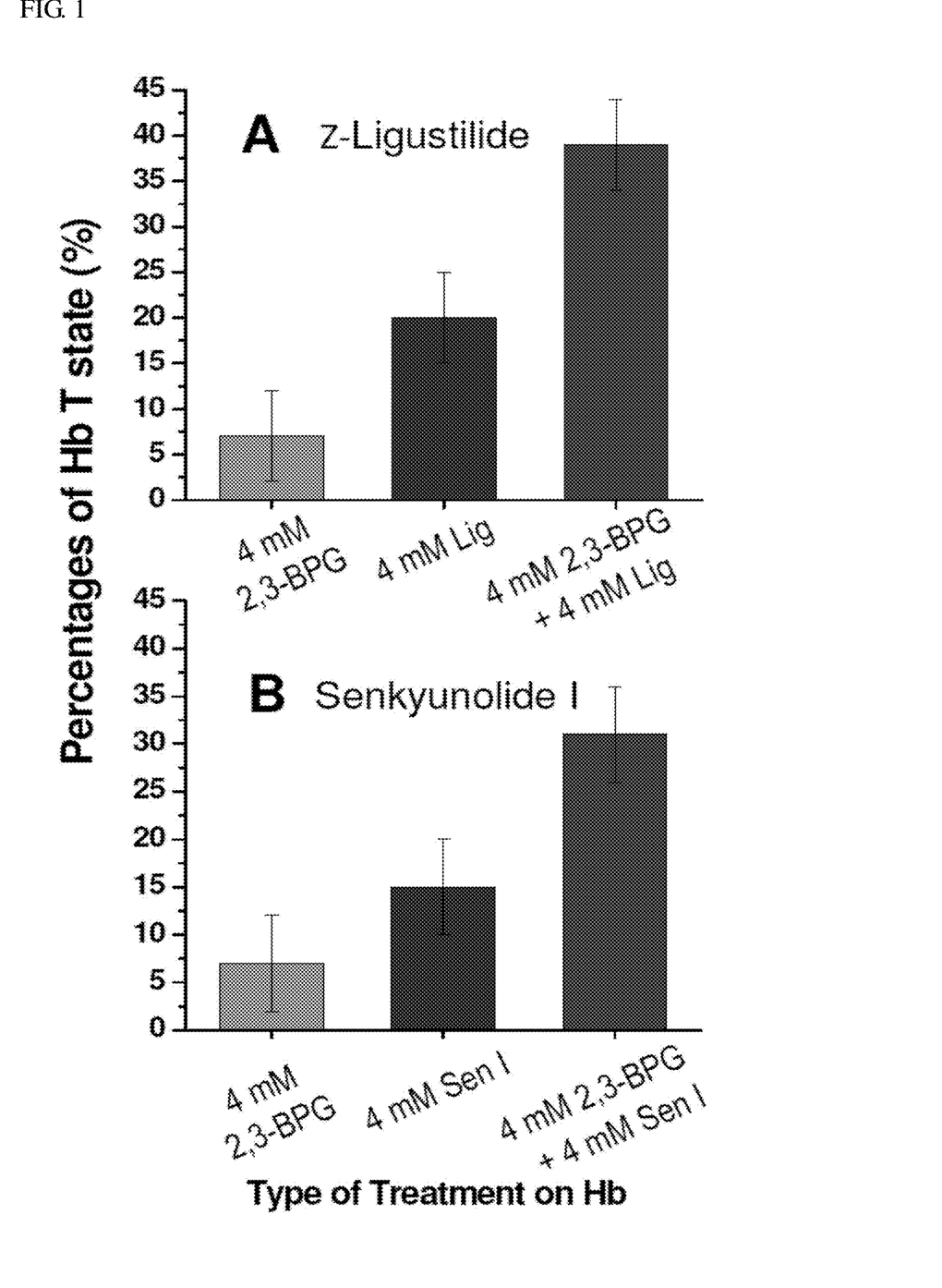
FIG. 1 shows the synergistic effect of phthalide compounds and 2,3-BPG; A: Z-ligustilide; B: senkyunolide I.

The phthalide compound provided by the present invention is not only used to substitute for or to supplement the 2,3-BPG of a treated subject, but also to cooperate with 2,3-BPG to provide a synergistic effect on increasing the oxygen release efficiency of hemoglobin (Hb) (as shown in FIG. 1).

Figure 2:
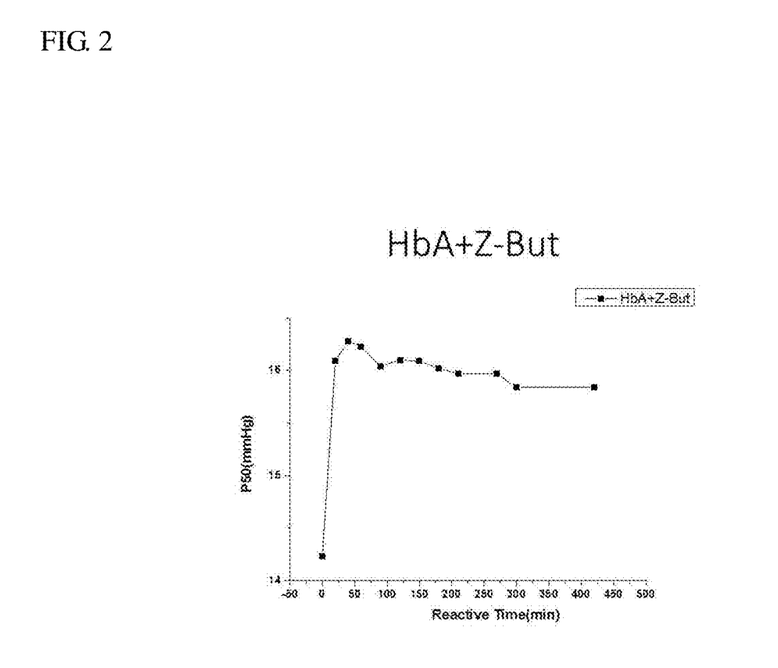
FIG. 2 shows the resulting $P_{50}$ values of Z-Butylidenephthalide, wherein in the shortest detection time frame (30 minutes), the phthalide compound can demonstrate an effect of increasing the oxygen release efficiency of hemoglobin (Hb).

The oxygen affinity of hemoglobin (Hb) is commonly characterized by $P_{50}$ value. The $P_{50}$ value is the required oxygen partial pressure to achieve 50% oxygen saturation of hemoglobin. The $P_{50}$ value of a normal adult is approximately 3.59 kPa (27 mmHg). An increased blood $PCO_2$, a decreased pH or an increased 2,3-BPG level in erythrocytes can all decrease the oxygen affinity of hemoglobin (Hb), so that the oxygen equilibrium curve shifts to the right and the $P_{50}$ value increases (as shown in FIG. 2); contrarily, when the oxygen affinity of hemoglobin (Hb) increases, the oxygen equilibrium curve shifts to the left and the $P_{50}$ value decreases.

Figure 3:
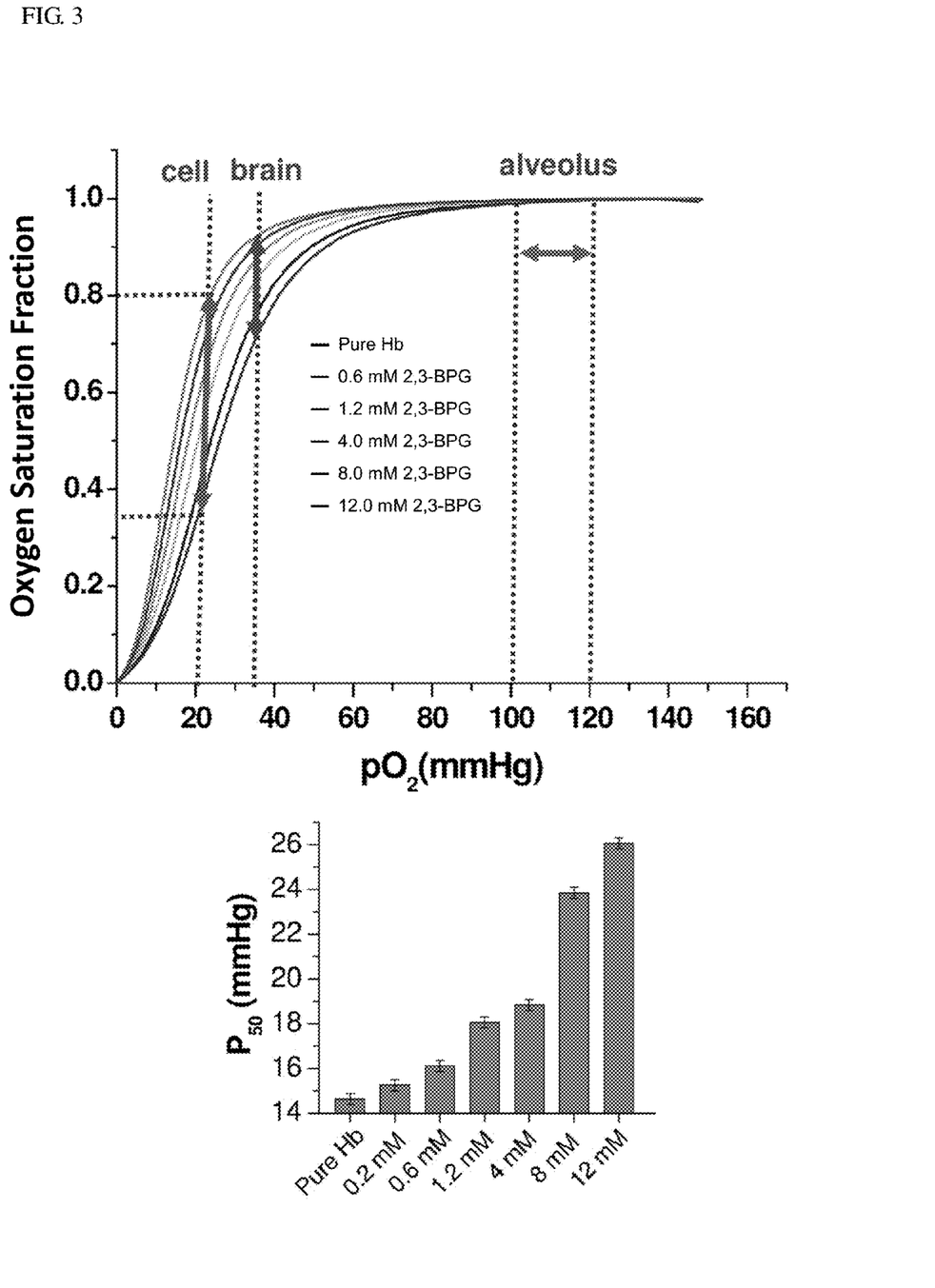
FIG. 3 shows oxygen equilibrium curves for hemoglobin (Hb) of various 2,3-BPG concentrations (0.2-12 mM) to illustrate that when hemoglobin (Hb) is modulated by 2,3-BPG, how the oxygen saturation fraction in human brain tissues, normal tissues and alveoli is changed with varying oxygen partial pressures. The oxygen equilibrium curves for hemoglobin (Hb) treated with various 2,3-BPG concentrations (0.2-12 mM) show that when the concentration of 2,3-BPG is higher, the oxygen equilibrium curve shifts more toward the right and the $P_{50}$ value is higher. The curves from the left to the right respectively represent: pure hemoglobin (Pure Hb) as the control group, 0.6 mM 2,3-BPG, 1.2 mM 2,3-BPG, 4.0 mM 2,3-BPG, 8.0 mM 2,3-BPG and 12.0 mM 2,3-BPG.

Under the normal physiological conditions, the $PO_2$ (oxygen partial pressure) of human cells is approximately 9.9-19 mmHg (*J. Cell. Mol. Med.*, 15, 1239-1253 (2011)). By observing from the oxygen equilibrium curves of hemoglobin the effect of varying concentrations of 2,3-BPG on the oxygen saturation fraction of hemoglobin at a fixed oxygen partial pressure (as shown in FIG. 3), the effect of 2,3-BPG on increasing the oxygen release efficiency of hemoglobin (Hb) is explicitly revealed. For example, when 12 mM of 2,3-BPG is administered to hemoglobin (the $6^{th}$ curve from the left, shown in FIG. 3), at a fixed oxygen partial pressure of 20 mmHg, the oxygen saturation fraction of hemoglobin (Hb) decreases from 80% where no 2,3-BPG is present in hemoglobin (Hb) (the first curve from the left, shown in FIG. 3) to 35%, indicating that the oxygen release efficiency of Hb increases from 20% to 65%.

Figure 4:
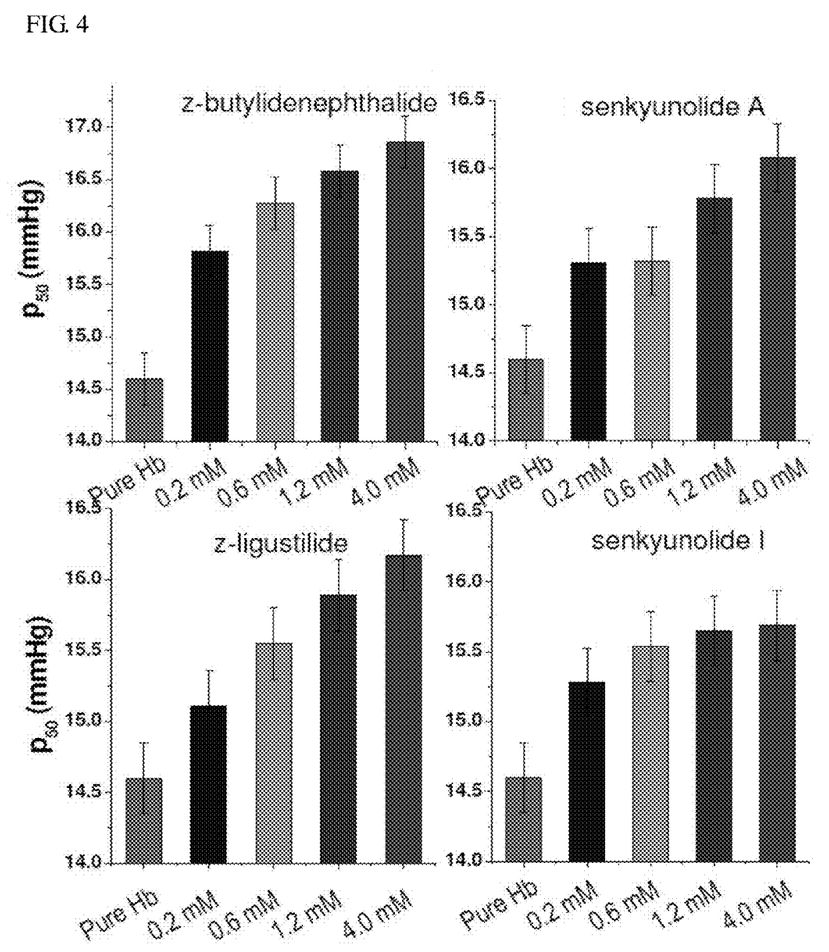
FIG. 4 shows that the $P_{50}$ value of hemoglobin (Hb) increases when the concentration of phthalide compounds increases, indicating that the oxygen affinity of hemoglobin (Hb) decreases and the oxygen release efficiency of hemoglobin (Hb) increases.

In one preferred embodiment, the phthalide compound can function similarly as 2,3-BPG to effectively increase the $P_{50}$ value of hemoglobin (Hb), that is, to lower the oxygen affinity of hemoglobin (Hb), and the higher the concentration of the phthalide compound, the higher the $P_{50}$ value and the lower the oxygen affinity are (as shown in FIG. 4).

Figure 5:
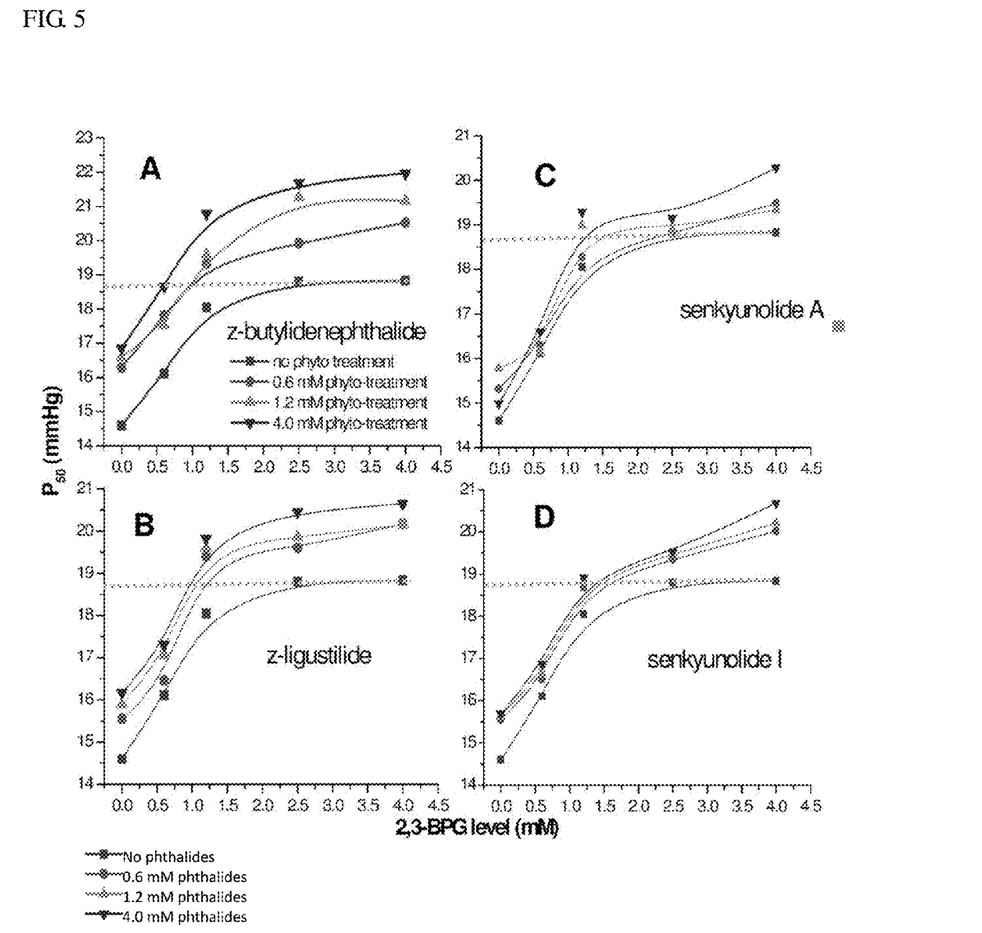
FIG. 5 shows that even at a low level of 2,3-BPG, phthalide compounds can help to modulate hemoglobin (Hb) such that Hb can reach a comparable $P_{50}$ value as that of hemoglobin under a normal level of 2,3-BPG.

In another embodiment, when no phthalide compound is administered to hemoglobin, approximately 4 mM of 2,3-BPG is required for hemoglobin (Hb) to achieve a $P_{50}$ value of 18.8 mmHg; but after a phthalide compound is administered to hemoglobin, only approximately 0.6-1.2 mM of 2,3-BPG is required to achieve the same or higher $P_{50}$ value (as shown in FIG. 5).

Figure 6:
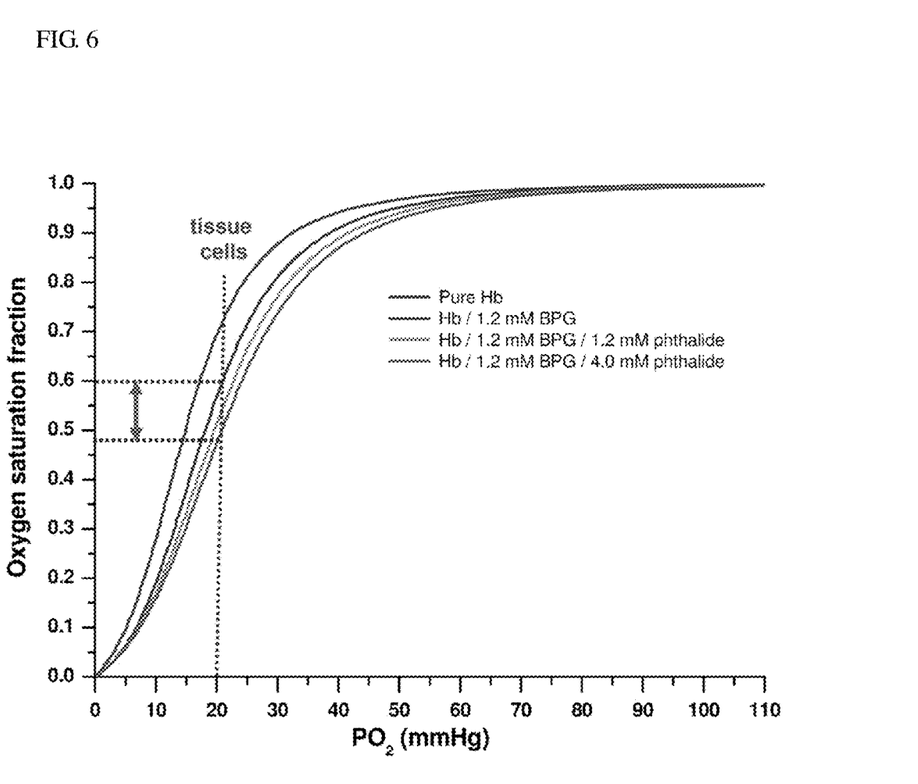
FIG. 6 shows that the oxygen equilibrium curves are modulated adjunctly by 2,3-BPG along with the phthalide compound, illustrating that the phthalide compound can cooperate with 2,3-BPG to decrease the blood oxygen saturation fraction and to increase the oxygen release efficiency when the oxygen partial pressure remains unchanged. The curves from the left to the right respectively represent: pure hemoglobin (Pure Hb) as the control group, 1.2 mM 2,3-BPG, 1.2 mM 2,3-BPG and 1.2 mM phthalide compound, and 1.2 mM 2,3-BPG and 4.0 mM phthalide compound.

In another embodiment, as shown in FIG. 6, under the condition where $PO_2$=20 mmHg and 1.2 mM 2,3-BPG is administered to hemoglobin, the oxygen saturation fraction is approximately 60%, but after an additional phthalide compound is administered, the oxygen saturation fraction decreases to approximately 47%, indicating that the oxygen release efficiency increases from 40% to 53%. Therefore, it confirms that phthalide compound is able to cooperate adjunctly with 2,3-BPG to allow the treated subject to release more oxygen from hemoglobin while keeping the oxygen partial pressure remains unchanged.

In another embodiment, 2,3-BPG is used together with the phthalide compound for preparing a drug and for being co-administered to a subject, wherein the methods for administering the drug comprises injection.

In another embodiment, the method of present invention is to additionally administer 2,3-BPG to a subject in need thereof.

Accordingly, the method of the present invention is to substitute for the hyperbaric oxygen therapy to alleviate hypoxia by using a phthalide compound; by shifting an oxygen equilibrium curve of hemoglobin (Hb) to the right to increase oxygen transportation and oxygen release efficiency of hemoglobin (Hb), the common adverse side effects of the hyperbaric oxygen therapy, such as barotrauma, decompression sickness and oxygen poisoning, are prevented. The phthalide compound provides a synergistic effect with 2,3-BPG to increase the oxygen release efficiency of hemoglobin (Hb).

EXAMPLES

The present invention may be embodied in different forms and is not limited by the examples mentioned in the following text. Those of ordinary skill in the art will recognize that many obvious modifications may be made thereto without departing from the sprit or scope of the present invention.

The examples and figures mentioned in the following text are used to illustrate the technical content, characteristics and advantages of the present invention and are not used to limit the present invention.

Figure 7A:
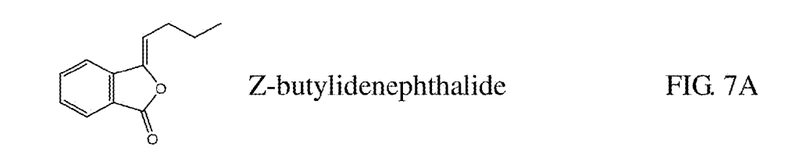
FIGS. 7A-7L show the chemical structures of twelve phthalide compounds; 7A: Z-butylidenephthalide; 7B: Z-ligustilide; 7C: senkyunolide A; 7D: senkyunolide H; 7E: senkyunolide I; 7F: senkyunolide F; 7G: E-butylidenephthalide; 7H: E-ligustilide; 7I: 3-butylphthalide; 7J: 3-butylidene-4-hydrophthalide; 7K: 6,7-dihydroxyligustilide; 7L: 6,7-epoxyligustilide.
Figure 7B:
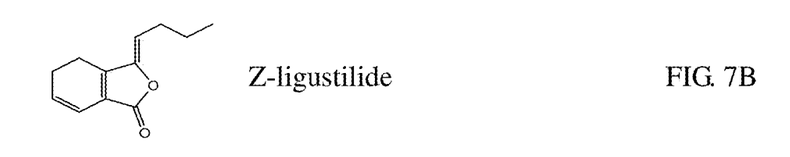
Figure 7C:
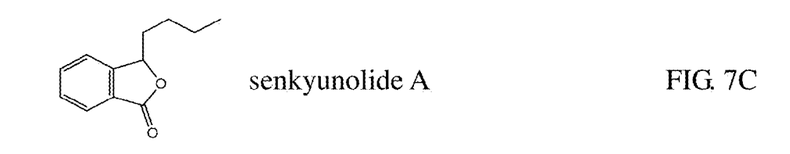
Figure 7D:
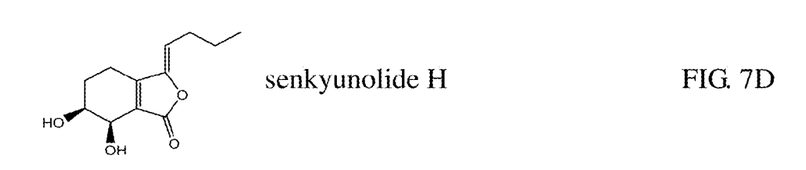
Figure 7E:
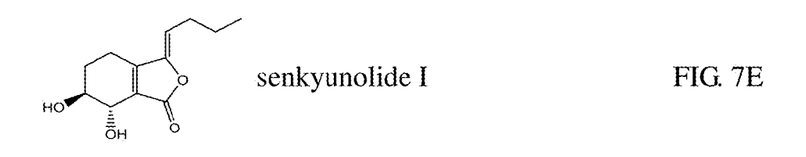
Figure 7F:
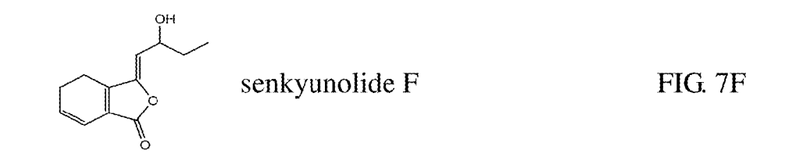
Figure 7G:
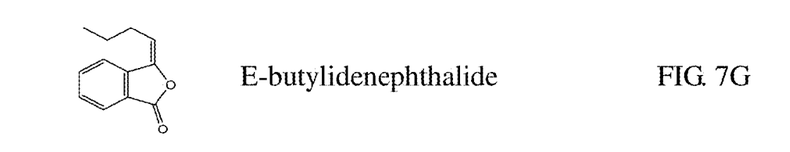
Figure 7H:
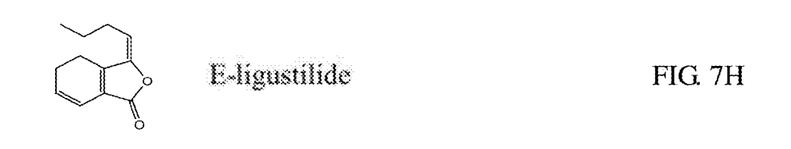
Figure 7I:
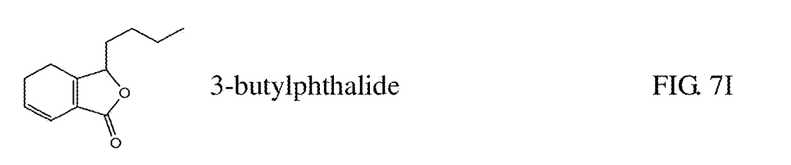
Figure 7J:
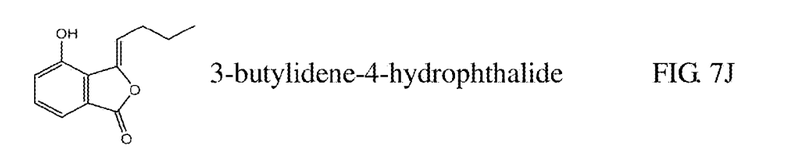
Figure 7K:
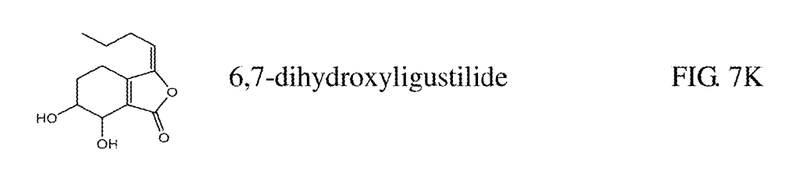
Figure 7L:
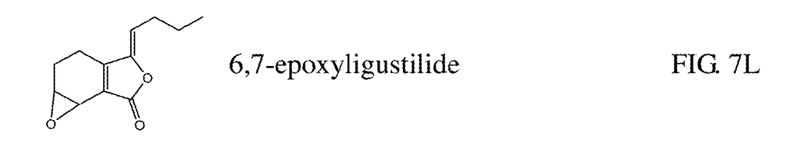

The phthalide compound provided by the present invention could be any compound exhibiting the structural characteristics of the phthalide compounds, such as, Z-butylidenephthalide (as shown in FIG. 7A), Z-ligustilide (as shown in FIG. 7B), senkyunolide A (as shown in FIG. 7C), senkyunolide H (as shown in FIG. 7D), senkyunolide I (as shown in FIG. 7E), senkyunolide F (as shown in FIG. 7F), E-butylidenephthalide (as shown in FIG. 7G), E-ligustilide (as shown in FIG. 7H), 3-butylphthalide (as shown in FIG. 7I), 3-butylidene-4-hydrophthalide (as shown in FIG. 7J), 6,7-dihydroxyligustilide (as shown in FIG. 7K) and 6,7-epoxyligustilide (as shown in FIG. 7L).

The oxygen affinity of hemoglobin (Hb) was commonly characterized by $P_{50}$ value. The $P_{50}$ value was the required oxygen partial pressure to achieve 50% oxygen saturation for hemoglobin. The $P_{50}$ value of a normal adult is approximately 3.59 kPa (27 mmHg). An increased blood PCO2, a decreased pH or an increased 2,3-BPG concentration in erythrocytes could decrease the oxygen affinity of hemoglobin (Hb), as a result, the oxygen equilibrium curve shifted to the right and the $P_{50}$ value increased (as shown in FIG. 2); contrarily, when the oxygen affinity of hemoglobin (Hb) increased, the oxygen equilibrium curve shifted to the left and the $P_{50}$ value decreased.

Under the normal physiological conditions, the $PO_2$ (oxygen partial pressure) of human cells is approximately 9.9-19 mmHg (J. Cell. Mol. Med., 15, 1239-1253 (2011)). By observing from the oxygen equilibrium curves of hemoglobin the effect of varying concentrations of 2,3-BPG on the oxygen saturation fraction of hemoglobin at a fixed oxygen partial pressure (as shown in FIG. 3), the effect of 2,3-BPG on increasing the oxygen release efficiency of hemoglobin (Hb) is explicitly revealed. For example, when 12 mM of 2,3-BPG is administered to hemoglobin (the purple curve shown in FIG. 3), at a fixed oxygen partial pressure of 20 mmHg, the oxygen saturation fraction of hemoglobin (Hb) decreases from 80% where no 2,3-BPG is present in hemoglobin (Hb) (the gray curve shown in FIG. 3) to 35%, indicating that the oxygen release efficiency increases from 20% to 65%.

In one preferred embodiment, the phthalide compound could function similarly as 2,3-BPG to effectively increase the $P_{50}$ value of hemoglobin (Hb), that is, to lower the oxygen affinity of hemoglobin (Hb), and the higher the concentration of the phthalide compound, the higher the $P_{50}$ value and the lower the oxygen affinity are (as shown in FIG. 4).

In another embodiment, when no phthalide compound was administered to hemoglobin, approximately 4 mM of 2,3-BPG was required for hemoglobin (Hb) to achieve a $P_{50}$ value of 18.8 mmHg; but after a phthalide compound was administered to hemoglobin, only approximately 0.6-1.2 mM of 2,3-BPG was required to achieve the same or higher $P_{50}$ value (as shown in FIG. 5).

In another embodiment, as shown in FIG. 6, under the condition where $PO_2$=20 mmHg and 1.2 mM 2,3-BPG was administered to hemoglobin, the oxygen saturation fraction is approximately 60%, but after an additional phthalide compound was administered, the oxygen saturation fraction decreased to approximately 47%, indicating that the oxygen release efficiency increased from 40% to 53%. Therefore, it confirmed that phthalide compound was able to cooperate adjunctly with 2,3-BPG to allow the treated subject to release more oxygen from hemoglobin while keeping the oxygen partial pressure remains unchanged.

In one example, as known from the resulting $P_{50}$ values, in the shortest detection time frame (30 minutes), the phthalide compound was able to show an effect of increasing the oxygen release efficiency of hemoglobin (Hb).

In one example, the phthalide compound could be used together with other compounds which were capable of stabilizing the oxygen-carrying hemoglobin (Hb) in the T form and effectively lowering the oxygen affinity of hemoglobin (Hb) in order to increase the oxygen release efficiency of hemoglobin (Hb) of a treated subject.

In another example, 2,3-BPG was additionally co-administered along with the phthalide compound to a subject, wherein the methods for administering comprised oral administration, injection and inhalation of aerosolized medication.

In another example, the phthalide compound was used together with 2,3-BPG for preparing a drug and for being administered to a subject treated by the hyperbaric oxygen therapy or a subject who needed to be treated by the hyperbaric oxygen therapy. In another preferred example, the phthalide compound was administered to a subject to adjunctly cooperate with the hyperbaric oxygen therapy, wherein the methods for administering the phthalide compound comprised oral administration, injection and inhalation of aerosolized medication, in order to reduce the chamber pressure in hyperbaric oxygen therapy and minimize the pressure difference of oxygen partial pressure among tissues.

In summary, the present invention provided a method for substituting for or acting with the hyperbaric oxygen therapy to improve hypoxia by using a phthalide compound, wherein the phthalide compound was able to increase the oxygen release efficiency of hemoglobin (Hb) of a treated subject. The phthalide compound was used to substitute for or act with 2,3-BPG to achieve the effect of increasing the oxygenation level of tissue cells, improving hypoxia and preventing the adverse side effects of the conventional hyperbaric oxygen therapy by shifting the oxygen equilibrium curves of hemoglobin (Hb) to the right when the oxygen partial pressure remained unchanged or was not excessively increased.

What is claimed is:

1. A method for substituting for or acting with a hyperbaric oxygen therapy (HBOT) to treat hypoxia, comprising the step of: administering a phthalide compound in combination with 2,3-bisphosphorglycerate to a subject in need thereof to increase oxygen release efficiency of hemoglobin (Hb) in the subject, wherein the subject is a subject treated by the hyperbaric oxygen therapy or a subject who needs to be treated by the hyperbaric oxygen therapy, wherein the phthalide compound is selected from the group consisting of Z-butylidenephthalide, Z-ligustilide, senkyunolide A, senkyunolide H, senkyunolide I, senkyunolide F, E-butylidenephthalide, E-ligustilide, 3-butylphthalide, 3-butylidene-4-hydrophthalide, 6,7-dihydroxyligustilide and 6,7-epoxyligustilide.

2. The method of claim 1, wherein the phthalide compound provides a synergistic effect with the 2,3-bisphosphorglycerate in the subject on increasing the oxygen release efficiency of hemoglobin (Hb).

3. The method of claim 1, wherein methods for administering the drug comprises oral administration, injection or inhalation of aerosolized medication.

* * * * *